(12) United States Patent
Laramay et al.

(10) Patent No.: US 8,273,426 B1
(45) Date of Patent: Sep. 25, 2012

(54) ENCAPSULATED COMPOSITIONS

(75) Inventors: Steven B. Laramay, Mesquite, TX (US); James J. Lavene, Rockwall, TX (US)

(73) Assignee: Fritz Industries, Inc, Mesquite, TX (US)

( * ) Notice: Subject to any disclaimer, the term of this patent is extended or adjusted under 35 U.S.C. 154(b) by 1144 days.

(21) Appl. No.: 11/651,895

(22) Filed: Jan. 10, 2007

(51) Int. Cl.
*B29D 22/00* (2006.01)
*B32B 5/16* (2006.01)

(52) U.S. Cl. ...................................... 428/35.7; 428/407

(58) Field of Classification Search .................. 428/357, 428/35.7, 402, 403, 407
See application file for complete search history.

(56) References Cited

U.S. PATENT DOCUMENTS

| | | | | |
|---|---|---|---|---|
| 4,459,398 A | * | 7/1984 | Dearlove et al. ................. | 528/1 |
| 4,741,401 A | | 5/1988 | Walles et al. .................. | 166/300 |
| 4,756,844 A | | 7/1988 | Walles et al. ................... | 252/95 |
| 4,919,209 A | | 4/1990 | King ............................. | 166/300 |
| 4,923,753 A | | 5/1990 | Walles et al. ............ | 428/402.24 |
| 5,173,526 A | | 12/1992 | Vijayendran et al. ......... | 524/457 |
| 5,373,901 A | | 12/1994 | Norman et al. ................. | 166/300 |
| 5,756,689 A | * | 5/1998 | Busman et al. .................. | 534/560 |
| 6,279,656 B1 | * | 8/2001 | Sinclair et al. ................. | 166/310 |
| 6,444,316 B1 | | 9/2002 | Reddy et al. .................. | 428/407 |
| 6,527,051 B1 | | 3/2003 | Reddy et al. .................. | 166/300 |
| 6,554,071 B1 | | 4/2003 | Reddy et al. .................. | 166/293 |
| 7,066,258 B2 | * | 6/2006 | Justus et al. .................. | 166/276 |
| 7,179,485 B1 | * | 2/2007 | Schneider et al. ............ | 424/451 |

FOREIGN PATENT DOCUMENTS

EP        1 166 866 A2    1/2002
WO    WO 2005/017313 A1   2/2005

* cited by examiner

*Primary Examiner* — Rena Dye
*Assistant Examiner* — James Yager
(74) *Attorney, Agent, or Firm* — Thomas R. Weaver

(57) ABSTRACT

A capsule having a reactive chemical enclosed in the hollow interior thereof, and at least one coating in direct contact with and surrounding the reactive chemical, wherein the coating is a heat-cured thermosetting synthetic resin. The capsule can also include a second coating which is in direct contact with and surrounds the heat-cured thermosetting synthetic resin. The reactive chemical is not reactive with, soluble in or a solvent for the coating, or coatings, which surround the reactive chemical in the hollow interior of the capsule. The coating material is not soluble in water, but is permeable to water.

21 Claims, No Drawings

ENCAPSULATED COMPOSITIONS

BACKGROUND OF THE INVENTION

1. Technical Field of the Invention

This invention relates to a composition comprised of a water soluble, particulate material confined in and surrounded by a coating which is permeable to water, but which is not water soluble. The invention also relates to a particulate reactive chemical confined in and surrounded by a coating which directly contacts the confined particulate reactive chemical. The invention further relates to a water soluble, particulate, reactive chemical confined in and surrounded by a coating comprised of an interior coating, which directly contacts the confined chemical, and an exterior coating. The invention particularly pertains to the chemical nature of the composition employed to produce the coating which directly contacts the particulate reactive chemical. The invention further pertains a method of making the composition. The invention still further pertains to the release of the particulate reactive chemical from the composition.

2. Description of the Prior Art and Problems Solved

The prior art has dealt with the problem of causing, or of creating the conditions to cause, a specified chemical to react in a specified environment or in a specified location at a specified time or over a specified period of time. This problem ordinarily stems from the need to initiate some chemical action in some desirable location prior to the start of, during or subsequent to the completion of some other action, and/or to cause the chemical action associated with a specified chemical to proceed over a desirable period of time. The related problems of controlling the time and place of reaction of a chemical, as well as the solutions thereto, have been variously referred to in the art as delayed release, continuous release and controlled release and are referred to as such herein.

The prior art has addressed the problems referred to above, and has developed various methods of controlling the introduction of an active chemical into reactive contact with an environment. Some solutions to the problems have involved preventing reactive contact of the active chemical with an environment followed by permitting reactive contact to occur at some later time. One of the methods developed features the steps of preventing the mentioned reactive contact by completely covering a small quantity of the active chemical with a material to confine the chemical in a capsule followed by introducing a number of such capsules into a designated environment wherein the chemical is released from the capsules to permit reactive contact.

The prior art has disclosed various different mechanisms for releasing an active chemical from a capsule into reactive contact with a designated environment. The disclosed release mechanisms have featured the use of capsules which are crushed to rapidly release the enclosed chemical; capsules which rupture, or burst, to rapidly release the enclosed chemical; capsules which dissolve or disintegrate to rapidly release the enclosed chemical; and capsules which do not rupture, but which rely on diffusion or permeation, to gradually release the enclosed chemical.

Chemicals known to have been released from a capsule by a controlled release mechanism have included medicines, pesticides, herbicides, cosmetics, laundry products, pigments, polymerization initiators, cross linking agents and viscosity reducing agents. A delayed and/or a continuous release of such chemicals from a confining material can offer the advantage of maximizing the effectiveness of the chemicals or of minimizing or eliminating undesirable chemical or physical results or both.

The differences between the various capsule-based controlled release methods of the prior art have resided in the nature of the material employed to form the coating or coatings on the capsule, and the specific mechanism of the controlled release. Examples of prior art methods involving a single coating are disclosed in various United States Patents including U.S. Pat. No. 4,756,844 (Walles I), U.S. Pat. No. 4,741,401 (Walles II), U.S. Pat. No. 4,923,753 (Walles III), U.S. Pat. No. 4,919,209 (King), and U.S. Pat. No. 5,373,901 (Norman et al).

Norman et al disclose a coating material comprising a partially hydrolyzed acrylic polymer crosslinked with either an aziridine prepolymer or a carbodiimide. The acrylic is defined as being comprised of a mixture of an unsaturated carboxylic acid and an alkyl acrylate or a methacrylate ester.

Reddy et al, in U.S. Pat. No. 6,444,316, disclose a dual coating system comprised of an interior coating in direct contact with the confined chemical, and an exterior coating in direct contact with the interior coating. The interior coating disclosed by Reddy et al is a dry hydrophobic product made from a material selected from the group consisting of styrene-butadiene rubber latex, waxes, oils, polybutylene and atactic polyolefins. According to Reddy et al, the interior coating may also be a sparingly soluble material. The exterior coating disclosed by Reddy et al is formed on the interior coating, and is a porous, cross-linked hydrophilic polymer comprised of partially hydrolyzed acrylic polymer which is cross-linked with either an aziridine prepolymer or a carbodiimide.

The principle difference between Reddy et al and Norman et al resides in the interior coating of Reddy et al. Norman et al and Reddy et al each disclose that their respective coating materials are applied to a particulate solid by a spray coating technique, referred to as a fluidized bed process. Thus, an aqueous solution of the coating material is sprayed on a particulate solid while the particulate is being fluidized by a hot gas such as air or nitrogen. The hot gas evaporates water from the aqueous solution leaving a dry porous membrane or film of the coating material on the particulate solid.

The patent art referred to above all disclose capsules containing reactive chemicals and the methods of releasing the chemicals from the capsules to enable the confined chemicals to react with a composition in contact with the exterior of the capsules. The disclosed chemicals range from those which treat water based liquids to those which treat oil based liquids. Walles I discloses an encapsulated bleach as a laundry detergent additive. The inventions of Walles II, King and Norman et al disclose an encapsulated breaker for a fracturing fluid in a subterranean formation. Walles III discloses an encapsulated acid. Reddy et al disclose encapsulated cement set time additives and strength accelerating agents, and encapsulated solvents for drilling fluid filter cake. Reddy et al disclose that their invention enables the successful encapsulation of calcium chloride, and other similar salts, acid and acid forming chemicals.

An important, if not the essential, feature of a method of controlling the release of a chemical composition from a capsule is the timing of the release. This feature can be illustrated in connection with the release of a chemical from a capsule to reduce the viscosity of a fracturing fluid subsequent to the performance of a fracturing treatment of a subterranean formation. Reducing the viscosity of a fracturing fluid is referred to in the art as "breaking" and the viscosity reducing chemical is referred to as a "breaker." For reasons well known in the fracturing art, it is desirable that a fracturing fluid have a high viscosity during the performance of the fracturing process, but a low viscosity subsequent to the performance of the process. In this regard, a desired high viscosity is preferably to be observed in the vicinity of the subterranean formation to be treated and a desired low viscosity is also preferably to be observed in the vicinity of the subterranean formation, wherein the high viscosity condition occurs prior to and during the performance of the fracturing treatment and the low viscosity condition occurs subsequent to the performance of the fracturing treatment.

Breakers, upon reactive contact with the fracturing fluid, can effectively produce the desired reduction of viscosity of the fluid, but the timing of the break, that is, when the break occurs, is of critical importance. Breakers, upon reactive contact with the fracturing fluid, begin to reduce the viscosity of the fluid. Accordingly, the problem to be solved is how to intimately mix the breaker with the fracturing fluid to enable contact with the fluid, while at the same time delaying actual reactive contact. This problem has been addressed and solved by placing the breaker in a capsule, the wall of which is a coating which operates to shield the fracturing fluid from contacting the breaker. The capsule containing the breaker is then intimately mixed with the high viscosity fluid, and the coating, by one of the mentioned mechanisms, functions to release the breaker to enable reactive contact between the breaker and the fluid at some future time. The breaking of fracturing fluids and the use of encapsulated breakers to perform the task are subjects discussed in Norman et al.

An important property of the coating composition is its ability to resist a caustic environment, either acid or base, exhibited by the chemical enclosed in, and, thus, in contact with, the interior surface of the coating composition, and by the chemical in contact with the exterior surface of the coating composition. The sensitivity of the coating composition to a caustic environment is the subject of the disclosure of Walles III. A capsule constructed of a confining material which will function to hold and maintain diverse chemicals, such as, organic and inorganic caustics, salts and oxidizers, and which will also function to release the chemicals at some desirable time is desired by the art.

DISCLOSURE OF INVENTION

1. Summary of the Invention

This invention is an article of manufacture, a method of making the article, and a method of using the article to treat a chemical environment in contact with the exterior of the article. The article is a capsule having a hollow interior containing a water-soluble, reactive chemical enclosed in the interior of the capsule by a wall comprised of a coating which is permeable to water or an aqueous solution. The permeable wall of the capsule can be a single coating structure, and it can be a dual coating structure comprised of a first coating and a second coating.

The chemical composition employed to make the single coating structure is also the chemical composition employed to make the first coating of the dual coating structure. Accordingly, the chemical nature of the single coating is identical to the chemical nature of the first coating, each of which is the heat-cured result of a material referred to herein as the first chemical composition. The interior of the cured first chemical composition is in direct contact with the reactive chemical enclosed in the interior of the capsule, and, in the case of the dual coating structure, the exterior of the cured first chemical composition is in direct contact with the interior of the second coating. The chemical nature of the second coating, the exterior coating, is referred to herein as the second chemical composition. The second chemical composition is not the same as the first chemical composition.

The first chemical composition is selected from the group consisting of aromatic and aliphatic thermosetting synthetic resins. The thermosetting synthetic resin, in one embodiment, is comprised of two six member aromatic rings connected by an aliphatic group, wherein hydrogen atoms in each ring can be substituted with a reactive group. In one aspect, each aromatic ring consists of six carbon atoms connected by an aliphatic chain of carbon atoms. In a second aspect, each aromatic ring consists of three carbon atoms and three nitrogen atoms connected by an aliphatic chain containing carbon atoms and nitrogen atoms, wherein hydrogen atoms in each ring can be substituted with reactive groups containing nitrogen and carbon.

It is known that a thermosetting synthetic resin is a synthetic polymeric compound which solidifies or "sets" irreversibly when heated. This setting property, which is also called curing, is ordinarily associated with a cross-linking reaction of the molecular constituents of the polymer. In some cases the thermosetting synthetic resin, as defined herein, includes a curing agent to promote the cross-linking reaction. The thermosetting resin, after setting, forms a permanent, durable, heat resistant product. In this regard recall the previous statement that the single coating is identical to the first coating, each of which is the heat-cured result of the first chemical composition.

2. Description of the Preferred Embodiments

The article of this invention is a capsule containing a water-soluble, reactive chemical enclosed in the interior of the capsule by a wall comprised of a coating which is permeable to water or an aqueous solution. The permeable wall of the capsule can be a single coating structure, and it can be a dual coating structure comprised of a first coating and a second coating. In the single coating structure the interior of the coating is in contact with the chemical enclosed in the interior of the capsule, and the exterior of the coating is in contact with the chemical environment to be treated by the reactive chemical enclosed in the interior of the capsule. In the dual coating structure the first coating is the interior coating, and is in direct contact with the chemical enclosed in the interior of the capsule, and the second coating is the exterior coating, and is in direct contact with the chemical environment to be treated by the reactive chemical enclosed in the interior of the capsule.

The first chemical composition can be made by combining a base compound, a reactant and, if required, a curing agent. To be specific, the term base compound, as used herein, means phenol, an epoxide or melamine. The term reactant means an aldehyde, a polyol or an alcohol. The term curing agent means an amine.

The chemical composition employed in the single coating structure is also the chemical composition employed as the first coating in the dual coating structure. The chemical nature of the single coating is, thus, identical to the chemical nature of the first coating, each of which is the heat-cured result of a thermosetting synthetic resin which is referred to herein as the first chemical composition. Accordingly, the interior of the cured first chemical composition is in direct contact with the reactive chemical enclosed in the interior of the capsule, and, in the case of the dual coating structure, the exterior of the cured first chemical composition is in direct contact with the interior of the second coating.

The first coating, i.e., the heat-cured result of the first chemical composition, is present in the capsule in an amount in the range of from about 1 to about 28, and preferably in the range of from about 2 to about 16 percent by weight of the capsule.

The chemical nature of the second coating, the exterior coating, is referred to herein as the second chemical composition. The second chemical composition is not the same as the first chemical composition. The second coating is at least comprised of the mentioned second chemical composition, and it can be comprised of the second chemical composition in combination with a third chemical composition, in which case, second coating is a composite coating. When the second coating is a composite coating the second chemical composition forms a supporting matrix, and the third chemical composition is fixed in the supporting matrix.

Aromatic thermosetting synthetic resins useful herein as the first chemical composition can be comprised of two six member aromatic rings connected by an aliphatic group wherein hydrogen atoms in each ring can be substituted with a reactive group. Formula 1 is a general structure which represents such resins containing curing agents, where employed.

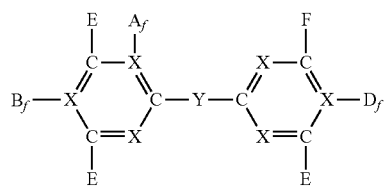

FORMULA 1 wherein: X is nitrogen (N) or carbon (C); E is the group

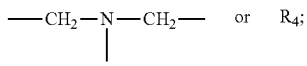

F is the group

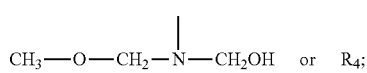

Y is the group

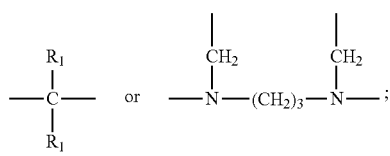

D is the group

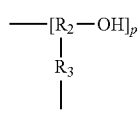

or OH; B is the group

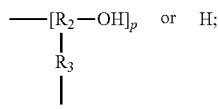

A is hydrogen (H) or a hydroxyl group (OH); $R_1$ is H or $CH_3$;

$R_2$ is the group

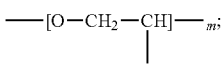

$R_3$ is the group $—[CH_2—CH_2—NH]—_n$;

$R_4$ is $CH_2$ or H; f is 0 or 1; p is 0 or 1; m is 0 or 1; and n is 0 to 3.

The first chemical composition is a polymer selected from a phenolic resin, an epoxy resin and a melamine resin. The term phenolic resin means any of several types of synthetic thermosetting resins obtained by the condensation of phenol, or a substituted phenol, with an aldehyde, such as formaldehyde, acetaldehyde and furfural. The term epoxy resin means any of several types of synthetic thermosetting resins obtained by the condensation of an epoxide and an aromatic or an aliphatic polyol to form a product which is subsequently combined with an amine. The term melamine resin means any of several types of synthetic thermosetting resins obtained by the reaction of melamine, an alcohol and an aldehyde.

Formula 2 represents the structure of phenolic resins and epoxy resins including curing agents, where employed. Formula 2 is obtained by substitution of Formula 1.

Thus, in Formula 1 if X is carbon (C), then f is 1, Y is the group

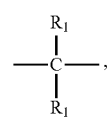

E is $R_4$ and F is $R_4$.

Accordingly, Formula 1 becomes Formula 2 as follows:

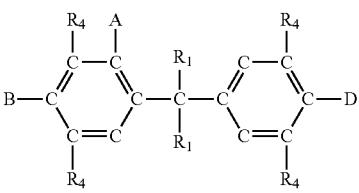

FORMULA 2

The phenolic resin produced by the reaction of phenol and formaldehyde is typical of the class of chemicals represented by Formula 2. Formula A, below, is a general structural formula for the phenolic resin produced by the reaction of phenol and formaldehyde.

Thus, in Formula 2, if $R_1$ is H, $R_4$ is $CH_2$, A is OH, D is OH and B is H, then Formula 2 becomes Formula A as follows:

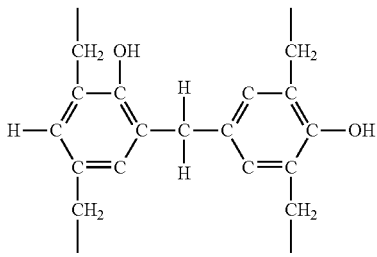

FORMULA A

Phenolic resins useful herein can be a precursor material. The phenolic resin precursor material, which can be a solid or a liquid, is made by the reaction of phenol and a quantity of aldehyde. The precursor is mixed, utilizing the pan coating method, with a curing agent, such as an aldehyde, prior to heating. During the heating step the mixture of precursor and curing agent is heated from room temperature to about 325° F. to fully cure the resin.

Phenolic resin precursors are commercially available from various manufacturers including Plastic Engineering Company, Sheboygan, Wis., under the trademark PLENCO, and Durex Corporation, Dallas, Tex., under the trademark DUREZ. The curing agent, which is also commercially available, can be an aldehyde, such as formaldehyde, or a material which produces an aldehyde upon heating.

In one aspect, the epoxy resin made by the reaction of an epoxide and an aromatic polyol which is subsequently cured by an amine is typical of the class of chemicals represented by Formula 2. An example of an epoxide useful to produce an epoxy resin useful herein is epichlorohydrin. An example of an aromatic polyol is a bisphenol, such as bisphenol A.

In a second aspect, the epoxy resin can be produced by the reaction of an epoxide and an aliphatic polyol which is subsequently cured by an amine. An example of an aliphatic polyol is glycerol.

Formula B, below, is a general structural formula for the epoxy resin produced by the reaction of epichlorohydrin and bisphenol A to form a product which is subsequently cured by diethylenetriamine.

Thus, in Formula 2, if $R_1$ is $CH_3$, $R_4$ is H, A is H, p is 1 (D is not OH and B is not H), m is 1 and n is 3, then Formula 2 becomes Formula B as follows:

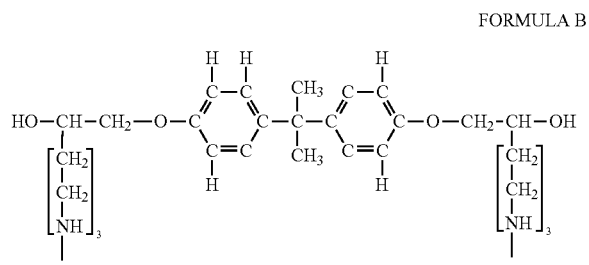

FORMULA B

The condensation product of an aromatic polyol and epichlorhydrin, which can be a liquid or a solid, is commercially available and is referred to in industry as an epoxy resin. The resin is mixed with a curing agent utilizing the pan coating method and then heated from room temperature to about 300° F. to fully cure the resin. This epoxy resin and the curing agent, a polyamine, can be obtained from the Dow Chemical Company, Midland, Mich., under the trademarks D.E.R. resin and D.E.H. hardener, respectively.

The term melamine resin means any of several types of synthetic thermosetting resins obtained by the reaction of melamine, an alcohol and an aldehyde. The melamine resin produced by the reaction of an alcohol, such as methyl alcohol, to form trimethylolmelamine which is then reacted with an aldehyde, such as formaldehyde, is typical of the class of chemicals represented by Formula 3 which is a general structural formula for the melamine resin produced by the reaction of melamine, formaldehyde and methanol.

Thus, in Formula 1 if X is nitrogen (N), then f is 0, Y is the group

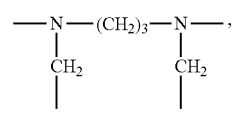

E is 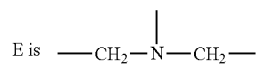

and F is

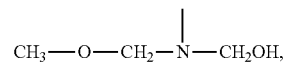

then Formula 1 becomes Formula 3 as follows:

FORMULA 3

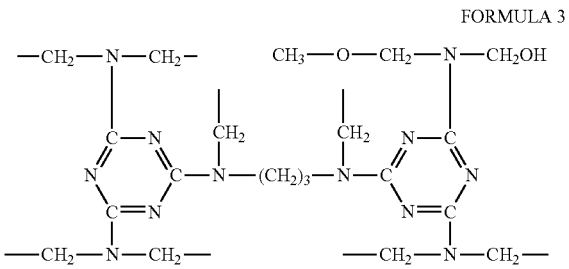

Melamine resins are commercially available from Cytec Industries, Inc., West Patterson, N.J., under the trademark CYMEL. The commercially available material and either an acid or base curing agent are mixed utilizing the pan coating method and then heated from room temperature to about 300° F. to fully cure the resin.

Particles of the chemical to be coated are contacted and physically mixed with the first chemical composition to enable the composition to coat the exterior of the particles. A mechanical mixing step, known as pan coating, is employed to apply the first chemical composition to the exterior of a quantity of chemical to be encapsulated. The coated particles are then heated. It is believed that heating at least accelerates the curing reaction, and may, in some cases, activate the reaction. The resulting coated article is dry, flowable and not sticky.

The second coating is comprised of a second chemical composition, and can be comprised of the second chemical combination in combination with a third chemical composition, in which case, the second coating is a composite coating. The second chemical composition can be any water based polymeric material such as a partially hydrolyzed acrylic polymer crosslinked with either an aziridine prepolymer or a carbodiimide. The acrylic polymer is comprised of a mixture of an unsaturated carboxylic acid and an alkyl acrylate or a methacrylate ester. Another example of the second chemical composition is a urethane/vinyl hybrid polymer.

Neither the second coating nor the composite coating is reactive with, soluble in or a solvent for the first coating, the chemical enclosed in the interior of the article or the chemical in contact with the exterior surface of the article.

When the second coating is a composite coating, the third chemical composition is a particulate solid and is different from the second chemical composition. The third chemical composition is hot reactive with, soluble in nor a solvent for the first coating, the chemical enclosed in the interior of the article, the second chemical composition, or the chemical in contact with the exterior surface of the article.

The chemical enclosed in the interior of the article can be substantially any water-soluble material which is not reactive with, soluble in nor a solvent for the first coating, the second coating or the composite coating. However, the encapsulated chemical is reactive with and is, thus, useful to alter the chemical and/or physical properties of the chemical in contact with the exterior surface of the article. The enclosed chemical can include enzymes, and organic and inorganic acids, bases, salts and oxidizing agents. The enclosed chemicals can be useful as medicines, pesticides, algaecides, herbicides, cosmetics, laundry products, pigments, polymerization initiators, cross linking agents and viscosity reducing agents. The enclosed chemicals can be an additive for adjusting the setting properties of hydraulic cement and can be a breaker for a fracturing fluid, wherein the breaker can be a chemical selected from water-soluble enzymes, and organic or inorganic acids, bases, salts and oxidizing agents.

The preferred exterior coating is a composite coating comprised of the second chemical composition, which forms a matrix, in combination with a third chemical composition, different from the second chemical composition, which is fixed in the matrix. The phrase "fixed in the matrix," when employed in connection with the third chemical composition, means that the third chemical composition, while being firmly attached to the matrix, can be completely embedded within and, therefor, completely surrounded by, the matrix, or it can be partially embedded within and partially exposed at the interior surface or at the exterior surface of the matrix. The second chemical composition, which forms the supporting matrix of the composite coating, is not reactive with, soluble in or a solvent for the interior coating, the encapsulated chemical, the third chemical composition or the chemical in contact with the exterior surface of the capsule.

The second chemical composition, as disclosed in U.S. Pat. No. 5,373,901 (Norman et al) and in U.S. Pat. No. 6,444,316 (Reddy et al), can be a partially hydrolyzed acrylic polymer crosslinked with either an aziridine prepolymer or a carbodiimide. The acrylic polymer is comprised of a mixture of an unsaturated carboxylic acid and an alkyl acrylate or a methacrylate ester.

The second chemical composition also can be a urethane latex system and, more specifically, an aqueous polyurethane-vinyl polymer dispersion. The vinyl element preferred for use is acrylic in nature. Accordingly, the dispersion is more particularly referred to herein as a urethane/acrylic hybrid polymer. The aqueous polyurethane-vinyl polymer dispersion employed herein is disclosed in U.S. Pat. No. 5,173,526 to Vijayendran et al. According to Vijayendran et al, the polyurethane-vinyl polymer dispersion is prepared by the simultaneous polymerization of a vinyl monomer and chain extension of an isocyanate-terminated polyurethane prepolymer in the presence of water. More particularly, Vijayendran et al disclose that, "the aqueous polymer is prepared by (a) forming a carboxy-containing, water dispersible, isocyanate-terminated polyurethane prepolymer, (b) adding a vinyl monomer mixture which contains a polyethylenically unsaturated monomer to the prepolymer to make a prepolymer/monomer mixture, (c) adding a tertiary amine to the prepolymer/monomer mixture, (d) dispersing the prepolymer/monomer mixture in water, (e) adding an oil soluble free radical initiator and a chain extender to the aqueous dispersion, and (f) polymerizing the vinyl monomers and completing the chain extension of the prepolymer by heating the aqueous dispersion." The process is said to provide an intimacy of interaction that cannot be achieved by blending. Accordingly, the first material, as defined above, is not a mere blend of a polyurethane and an acrylic polymer.

A urethane/acrylic hybrid polymer dispersion useful herein is commercially available in the form of an aqueous polymer dispersion from Air Products and Chemicals, Inc., under the Hybridur family of trademarks, two of which are Hybridur 540 and Hybridur 580.

The aqueous polyurethane-vinyl polymer dispersion employed is disclosed in Vijayendran et al to be useful as a protective coating for a solid substrate. It is disclosed that the dispersion is applied to the substrate by conventional flexographic or gravure methods and that the finished product protects the substrate from solvents, corrodants, and abrasives and that it exhibits good gloss and flexibility. The mentioned solid substrates include paper, metals, plastics and wood.

The urethane/acrylic hybrid polymer can be cross linked with a polyaziridine, carbodiimides, epoxies or metal ion cross linkers. An example of a polyaziridine polymer useful herein is pentaerythritol-tris-[β-(aziridinyl)proprianate]. An example of a carbodiimide useful herein is 1,3-dicyclohexyl-carbodiimide. The urethane/acrylic hybrid polymer is preferably reacted with an aziridine cross linking agent to form the second chemical composition.

The third chemical composition is a particulate solid present in the composite coating in an amount in the range of from greater than about 0 to about 50, preferably 10 to about 40 and still more preferably from about 20 to about 30 percent particulate solid by total weight of composite coating. The particulate solid can have a size in the range of from about 1 to about 15 and preferably from about 2 to about 5 microns. The particle size of the particulate solid in the composite coating is preferably not less than 1 micron. In a manufacturing operation it is, of course, difficult to completely exclude all particulate solids having a size of less than 1 micron, however, it is preferred that concentration of particulate solids having a size less than 1 micron should not exceed about 25 percent by weight of particulate solids present in the composite coating.

The third chemical composition can include silica, calcium carbonate, titanium dioxide, barium sulfate, calcium sulfate, similar such materials and mixtures thereof.

The chemical encapsulated within the article of this invention can be substantially any water-soluble material selected from the group consisting of enzymes, and organic and inorganic acids, bases, salts and oxidizing agents. More specifically, the chemical compositions preferably include alkali, alkaline earth metal and ammonium halides, oxides, hydroxides, carbonates, bicarbonates, perborates, peroxides, percarbonates, bisulfates, bromates and sulfates. The encapsulated chemical can also include liquids which have been adsorbed on solid substrates, such as, diatomaceous earth and then encapsulated.

Specific examples of chemicals to be encapsulated include hemicellulase, sodium bisulfate, calcium chloride, lithium hydroxide, potassium carbonate, salts of phosphonic acid, sodium persulfate, ammonium persulfate, magnesium oxide, citric acid, fumaric acid, sodium citrate, sodium fumarate, polyglycolic acid, sulfamic acid, potassium bromate, sodium bromate and tetraethylpentamine.

In one embodiment, the chemical to be encapsulated can be a breaker for an aqueous fracturing fluid, examples of which include the oxidizing agents, sodium persulfate and potassium persulfate. In another embodiment, the chemical can be an aqueous viscosifying agent such as guar gum, hydroxy propyl guar, hydroxy ethyl cellulose and xanthan gum. In still another preferred embodiment, the chemical can be an additive for adjusting the setting properties of hydraulic cement such as accelerators, retarders and viscosifiers, examples of which include calcium chloride, calcium lignosulfonate and hydroxy ethyl cellulose. In yet another embodiment, the chemical can be a pH adjusting material such as lithium hydroxide and potassium carbonate.

A capsule having a dual coating structure is made in a two-step process in which the first step is defined herein as a pan coating process, and the second step is defined herein as a fluidized bed process.

In the pan coating process, the chemical to be encapsulated is thoroughly mixed with a thermosetting synthetic resin as previously described. The chemical to be encapsulated is in the form of a mass of solid particles, and the thermosetting synthetic resin can be in the form of a liquid or in the form of a mass of solid particles. There is no known limitation on the particle size of the chemical to be encapsulated, but a particle size in the range of from about 10 to about 100 mesh US Sieve series is conveniently employed. Thus, with respect to the above range, particles of a size which do not pass a 10 mesh screen and particles which do pass a 100 mesh screen are preferably not employed. To maintain product uniformity with respect to performance, the chemical, prior to encapsulation, is preferably sized to remove a substantial portion of any fines or agglomerations of chemical particles. In this manner, the thickness of the membrane wall of the capsules will have, within a relatively narrow range, a substantially uniform thickness and the capsules will exhibit generally uniform release control properties.

The mixing of the chemical to be encapsulated with the thermosetting synthetic resin is preferably conducted in a container equipped or associated with paddles and blades adapted to blend, stir and move a mass of solid particles. The mixing step is complete when the resulting particles produced in the mixing step are somewhat sticky and have an attraction each to the other, but the mixture is not liquid. The term of art employed to describe the condition of the finished mixture is "blocky."

When the mixing step is complete the resulting particulate mixture is heated until the mix is no longer "blocky." The heating is conducted at a temperature in the range of from about 60° to about 350° F. depending upon the resin and catalyst employed. At this point the pan coating process is complete, and the formed single coat capsules are dry, flowable and not sticky.

Upon completion of the pan coating process, an exterior coating can be applied to the exterior of the single coating capsules by the fluidized bed process, one version of which is referred to as the Wurster process and a modification thereof which employs a top spray method. Equipment employed to apply the exterior coating is available from Glatt Air Techniques, Inc. Ramsey, N.J. A specific apparatus available from Glatt Air Techniques is the WSG 5 fluidized bed coater.

In a preferred method of applying the exterior coat, the third chemical composition, that is, the particulate solid, is mixed with the second chemical composition, the urethane/acrylic hybrid in an amount greater than about 0 to about 50, preferably 10 to about 40 and still more preferably from about 20 to about 30 percent particulate solid by total weight of composite coating. The cross linker can then be admixed with the hybrid polymer and solid in an amount in the range of from about 0 to about 5, and preferably from about 1 to about 3, percent cross linker by weight of hybrid polymer. Thereafter, utilizing the fluidized bed process, the single coating capsule made by the pan coating process is introduced into a spray chamber and suspended therein by a flow of gas, such as air, while the mixture of hybrid polymer, solid and cross linker are sprayed against the suspended first capsule to thereby form a capsule having a dual coating structure. The combination of chemical to be encapsulated and composite coating is adjusted to produce a dual coating capsule having in the range of from about 10 to about 50, and preferably from about 20 to about 40 percent composite coating by weight of dual coating capsule.

Generally, a capsule of this invention is prepared having a membrane coating consisting of the interior coating and the exterior coating, for example the composite coating, wherein the membrane coating has sufficient thickness and permeability to obtain the desired controlled release of the encapsulated chemical to treat the chemical in contact with the exterior coating. The quantity and size of the particulate solid present, that is the third chemical composition, in the composite coating will significantly effect the permeability of the created membrane coating.

The particle size of the capsule varies depending upon the desired amount of encapsulated chemical to be released and the desired rate at which the chemical is to be released. For example, the thicker the membrane, generally the slower the release since it takes longer for an aqueous liquid in contact with the exterior surface of the capsule to diffuse, i.e., permeate, through the wall of the membrane to dissolve the agent and then diffuse, i.e., permeate, back through the membrane. This relationship, however, can be modified by changing the particle size of the third chemical composition. If the material to be treated by the encapsulated chemical is a fracturing fluid containing a proppant, then it is preferred that the particle size of the capsule be substantially equal to or smaller than the particle size the proppant.

In the method of operation, an aqueous liquid in contact with the exterior surface of the capsule gradually passes, by diffusion, through the coating into the interior of the capsule and therein contacts and dissolves the encapsulated chemical to form an aqueous solution. It is to be understood that the aqueous liquid in contact with the exterior surface of the capsule can be present in the contact location as a natural constituent of the environment or introduced into the environment prior to, together with or subsequent to the introduction of the capsule.

The solution formed within the capsule then gradually passes, by diffusion, from the interior of the capsule through the coating to the exterior of the capsule to there contact and react with the material to be treated.

The described operating mechanism, which consists in diffusion of an aqueous liquid in contact with the exterior of the capsule into the capsule and diffusion of a formed solution out of the capsule, requires an extended period of time to be completed to thereby avoid release of all of the encapsulated chemical over a very short span of time.

It is believed that the operating mechanism of this invention is driven by very small pressure differences between the interior and exterior of a capsule. Thus, when the pressure in the interior of the capsule is less than the pressure on the exterior of the capsule, the aqueous liquid passes through the membrane into the interior of the capsule to contact and dissolve the encapsulated chemical. Upon dissolution, pressure within the interior of the capsule increases to a value greater than the pressure on the exterior of the capsule. Accordingly, upon this pressure increase, the formed solution passes through the membrane to the exterior of the capsule. In some instances, depending upon the nature of the aqueous liquid and/or the nature of the encapsulated chemical, a gas may be produced within the interior of the capsule. It is believed that pressure produced by such gas does not cause the capsule to rupture, break, dissolve or disintegrate. The capsule remains intact during the entire diffusion process.

The particle size of the third chemical composition, which is fixed in the matrix, plays an important role in the diffusion process. In this regard, it is believed that capsules which contain particles having a size of less than about 1 micron, i.e., submicron particles, do not operate to dissipate internal pressure, generated as described above, at a rate sufficiently great to prevent rupture of the capsule. Capsules which contain particles having a size of 2 microns and greater, preferably about 5 microns, fixed in the matrix, do operate to dissipate internal pressure at a rate sufficient to prevent rupture of the capsule.

The capsule of this invention functions to slowly release all of the encapsulated chemical over an extended period of time as contrasted with a rapid release of all of the encapsulated agent over a very short period of time. The capsule operates as stated, without change in the desired rate of release of the encapsulated composition, in the presence of liquids at temperatures in the range of from about 50 to about 325° F. and at pH values in the range of from about 2 to about 11.

EXAMPLES

Example 1

Particles of anhydrous citric acid were mixed with an uncured phenolic resin. The mixture of citric acid and uncured resin was heated to cure the resin to thereby produce capsules consisting of citric acid coated by the cured resin. For purposes of identification, these capsules having a single coating of cured phenolic resin were designated as Capsules A.

Three batches of Capsules A were prepared for testing. Each test batch weighed about 1760 grams, accordingly, a total of about 5280 grams of Capsules A were prepared for subsequent testing.

A four step process was employed to prepare each test batch. In the first step, about 1500 grams of anhydrous citric acid having a particle size in the range of from 10 to about 50 mesh US Sieve Series were heated in an oven to a temperature of about 250° F.

In the second step, the heated, acid was placed in a 5 quart mixing bowl equipped with a paddle having the capability of mixing and stirring particulate solids. The mixer employed was a Kitchen Aid Model KV25G. The mixer was then started and, while mixing and heating, about 88.1 grams of powdered uncured phenolic resin and about 7.65 grams of an atomized wax-free flow additive were added to the mixer containing the heated acid. The phenolic resin employed was available from Plastic Engineering Company of Sheboygan, Wis., and the flow additive was available from Lonza, Inc. of Fairlawn, N.J. The mixture was heated and stirred until it became blocky and then it was allowed to cool until it became free and flowing. The heating, mixing and cooling procedure was repeated until the mixture could be heated to 275° F. without becoming blocky. At this point the phenolic resin was considered to be cured. The resulting material, which weighed about 1595.75 grams, was passed through a 10 US Mesh screen which produced a finished product weighing about 1500 grams.

In the third step, the 1500 gram product from the second step was heated to a temperature of about 240° F. at which point the procedure of the second step was repeated except that 100.1 grams of powdered uncured phenolic resin and about 8.72 grams of flow additive were employed. Upon curing, the resulting material, which weighed about 1698.72 grams, was passed through a 10 US Mesh screen which produced a finished product weighing about 1695 grams.

In the fourth step, the 1695 gram product from the third step was heated to a temperature of about 240° F. at which point the procedure of the second step was repeated except that 74.7 grams of powdered uncured phenolic resin and about 6.5 grams of flow additive were employed. Upon curing, the resulting material, which weighed about 1776.2 grams, was passed through a 10 US Mesh screen which produced a finished product Weighing about 1760 grams.

It is evident that the process employed a total of about 1500 grams of active citric acid, about 262.9 grams of uncured phenolic resin and about 22.87 grams of flow additive. It was calculated that the product of the four-step process, Capsules A, included about 83.96 weight percent active citric acid and about 16.04 weight percent cured phenolic resin and flow additive.

Example 2A

This example describes the process employed to make a liquid dispersion of solids containing a cross-linked polyurethane and silica particles. For purposes of identification, the product of the process is referred to as polyurethane coating A.

Preparation of Polyurethane Coating A

1. About 2161.2 grams of water, about 84.8 grams of silicone defoamer and about 127.1 grams of silicone surface additive were mixed with mild agitation in a 2 gallon bucket until the surfactants were dispersed in the mixture. The defoamer was identified as BYK-024 and the surface additive was identified as BYK-333, respectively, with each being available from BYK-Chemie.

About 2177.1 grams of aqueous hybrid polyurethane dispersion was introduced into the surfactant dispersion. The aqueous hybrid polyurethane dispersion, which contained about 40 weight percent polymer solids, was available from Air Products and Chemical, Inc., under the trademark HYBRIDUR 540, and is described in U.S. Pat. No. 5,173,526 to Vijayendran et al. Agitation of the mixture was continued until the contents were dispersed.

At that point the dispersion was mixed with a high shear mixer while about 2,542.6 grams of 5-micron silica was slowly added to the mass of material. Mixing was continued until the silica was completely dispersed. The high shear mixer employed was available from Charles Ross and Sons Mixer Company, and the silica was available from US. Silica under the trademark MIN-U-SIL 5. The use of a mixture of hybrid polyurethane dispersion and silica is described in U.S. patent application Ser. No. 09/770,931 filed Jan. 26, 2001.

The mixture of polyurethane and silica was placed in a 5-gallon pail. An air mixer was employed to stir the mixture in the pail at a rate sufficient to form a vortex while an additional quantity of about 12,654.8 grams of the mentioned aqueous hybrid polyurethane dispersion was added. After about 5 minutes of mixing, 889.9 grams of coalescent solvent, GLYCOL ETHER PNB available from Chem Central, was added. The mixing rate was adjusted to maintain the vortex. After about 30 minutes of mixing, about 91.5 grams of 29 weight percent aqueous ammonia was added and mixing was continued for about 30 minutes. The resulting precursor product was set aside and allowed to stand at least over night.

It is evident that preparation of the precursor product employed about 20,729 grams of ingredients, of which about 8713.795 grams were considered to be solids. It was, accordingly, calculated that the product included about 42.04 weight percent solids.

2. After the period of standing, 2309.5 grams of the precursor product were combined with about 30 grams of a polyaziridine cross-linker and about 160.6 grams of water. The mixture was stirred for about 10 minutes to thereby prepare 2500.1 grams of polyurethane coating A. Polyurethane coating A was applied to Capsules A.

It was calculated that polyurethane coating A consisted of about 1000.84 grams of solid which was about 40.03 weight percent of the product.

Example 2B

This example describes the process employed to make a liquid dispersion of solids containing a cross-linked polyurethane and silica particles. For purposes of identification, the product of the process is referred to as polyurethane coating B.

Preparation of Polyurethane Coating B

After the period of standing, 6235.7 grams of the precursor product from Step 1 of Example 2A were combined with about 81 grams of a polyaziridine cross-linker and about 433.3 grams of water. The mixture was stirred for about 10 minutes to thereby prepare 6750.00 grams of polyurethane coating B. Polyurethane coating B was applied to anhydrous citric acid.

It was calculated that polyurethane coating B consisted of about 2702.28 grams of solid which was about 40.03 weight percent of the product.

Example 3

Capsules A were contacted with successive quantities of polyurethane coating A to place a coating of cross-linked polyurethane on Capsules A. The polyurethane coated products are referred to herein as Capsules A1, A2, A3 and A4. It is clear that Capsules A1, A2, A3 and A4 included a core of citric acid, an inner coating of cured phenolic resin and an outer coating of cross-linked polyurethane.

Application of Polyurethane Coating A to Capsules A

A. Capsules A1

A fluidized bed coating apparatus was used to apply 500 grams of polyurethane coating A to a total of 4800 grams of Capsules A. In this regard, 4800 grams of Capsules A were added to the product bowl of a WSG 5 fluidized bed coater available from Glatt Air Techniques equipped with a top spray insert. The spray head employed was a Schick Model 970 nozzle having a 1.2 mm insert available from Orthos Liquid Systems, Inc. An 80 mesh screen was inserted between the expansion chamber and the filter chamber of the coater.

Capsules A were fluidized in the coating apparatus with air heated to a temperature in the range of from about 90 to about 96° F. Polyurethane coating A was sprayed against the fluidized Capsules A through the spray head. The spray head pressure was about 37 psig, and the spray rate was about 40 grams per minute.

The spray was terminated when a total of 500 grams of polyurethane coating A had passed through the spray head. At this point 200 grams of the coated capsules, now referred to as Capsules A1, were removed from the coating apparatus for future testing.

It was calculated that the 500 grams of coating included a total of about 200.16 grams of solid which were deposited on the capsules. Accordingly, it was also calculated that Capsules A1 included about 80.6 weight percent active citric acid and about 19.4 weight percent total coating. Stated differently, Capsules A1 included about 80.6 weight percent active citric acid, about 15.4 weight percent phenolic inner coating and about 4 weight percent polyurethane outer coating.

After removal of the 200 gram sample of Capsules A1, the coating apparatus contained a total of about 4800.16 grams of Capsules A1.

B. Capsules A2

The quantity of Capsules A1 remaining in the coating apparatus were then sprayed with 521.7 grams of polyurethane coating A to thereby produce Capsules A2. The apparatus and conditions employed to produce Capsules A1 were used to produce Capsules A2.

The spray was terminated when a total of 521.7 grams of polyurethane coating A had passed through the spray head. At this point 200 grams of the coated capsules, now referred to as capsules A2, were removed from the coating apparatus for future testing.

It was calculated that the 521.7 grams of coating included a total of about 208.85 grams of solid which were deposited on the capsules. Accordingly, it was also calculated that Capsules A2 included about 77.24 weight percent active citric acid and about 22.76 weight percent total coating. Stated differently, Capsules A2 included about 77.24 weight percent active citric acid, about 14.75 weight percent phenolic inner coating and about 8.01 weight percent polyurethane outer coating.

After removal of the 200 gram sample of Capsules A2, the coating apparatus contained a total of about 4809.01 grams of Capsules A2.

C. Capsules A3

The quantity of Capsules A2 remaining in the coating apparatus were then sprayed with 546.4 grams of polyurethane coating A to thereby produce Capsules A3. The apparatus and conditions employed to produce Capsules A2 were used to produce Capsules A3.

The spray was terminated when a total of 546.4 grams of polyurethane coating A had passed through the spray head. At this point 200 grams of the coated capsules, now referred to as Capsules A3, were removed from the coating apparatus for future testing.

It was calculated that the 546.4 grams of coating included a total of about 218.73 grams of solid which were deposited on the capsules. Accordingly, it was also calculated that Capsules A3 included about 73.88 weight percent active citric acid and about 26.12 weight percent total coating. Stated differently, Capsules A3 included about 73.88 weight percent active citric acid, about 14.11 weight percent phenolic inner coating and about 12.01 weight percent polyurethane outer coating.

17

After removal of the 200 gram sample of Capsules A3, the coating apparatus contained a total of about 4827.74 grams of Capsules A3.

D. Capsules A4

The quantity of Capsules A3 remaining in the coating apparatus were then sprayed with 574.7 grams of polyurethane coating A to thereby produce Capsules A4. The apparatus and conditions employed to produce Capsules A3 were used to produce Capsules A4.

The spray was terminated when a total of 574.7 grams of polyurethane coating A had passed through the spray head. The temperature of the bed was permitted to increase to a temperature in the range of from about 105 to about 110° F. for about five minutes. At this point 200 grams of the coated capsules, now referred to as Capsules A4, were removed from the coating apparatus for future testing.

It was calculated that the 574.7 grams of coating included a total of about 230.06 grams of solid which were deposited on the capsules. Accordingly, it was also calculated that Capsules A4 included about 70.52 weight percent active citric acid and about 29.48 weight percent total coating. Stated differently, Capsules A4 included about 70.52 weight percent active citric acid, about 13.47 weight percent phenolic inner coating and about 16.01 weight percent polyurethane outer coating.

After removal of the 200 gram sample of Capsules A4, the coating apparatus contained a total of about 4857.8 grams of Capsules A4.

Example 4

Particles of anhydrous citric acid were mixed polyurethane coating B to thereby produce capsules comprising citric acid coated by cross-linked polyurethane. For purposes of identification, these capsules having a single coating of cross-linked polyurethane were designated as Capsules B. The weight of Capsules B included about 36 percent cross-linked polyurethane.

18

Application of Polyurethane Coating B to Citric Acid

The procedure and equipment described in Example 3 were employed to apply 6750 grams of polyurethane coating B to a total of 4800 grams of anhydrous citric acid having a size in the range of from 10 to about 50 mesh US Sieve Series.

The spray was terminated when a total of 6750 grams of polyurethane coating B had passed through the spray head. The temperature of the bed was permitted to increase to a temperature in the range of from about 105 to about 110° F. for about five minutes.

It was calculated that the 6750 grams of coating included a total of about 2702.28 grams of solid which were deposited on the citric acid. Accordingly, it was also calculated that Capsules B included about 63.98 weight percent active citric acid and about 36.02 weight percent polyurethane coating.

Example 5

Capsules A, A1, A2, A3, A4 and B were immersed in water to determine the release of citric acid from the capsules over a period of time.

Samples of each of Capsules A, A1, A2, A3, A4 and B were placed in water. The citric acid in each sample passed into the water over a period of time. The concentration of acid in the resulting solutions of citric acid in water increased with passage of time, wherein the concentration of acid in a solution was determined over intervals of time by measuring the electrical conductivity of the solution with an electrical conductivity meter. The meter had been previously calibrated by measuring the conductivity of solutions having known concentrations of citric acid.

The water solvent contained 0.1 weight percent nonylphenol. The tests were conducted at room temperature.

Tables

Table 1 is a summary of calculated results based on experimental quantities employed in Examples 1-4. The contents of Table 1 also summarize experimental quantities employed in Example 5 and calculated results based on such quantities. Table 2 is a summary of acid released from the capsules as a weight percent of acid in the samples tested.

TABLE 1

| DATA | | CAPSULES | | | | | |
|---|---|---|---|---|---|---|---|
| | | A | A1 | A2 | A3 | A4 | B |
| Total Grams (solids) | | 480.00 | 200.00 | 200.00 | 200.00 | 5057.80 | 7502.28 |
| Citric Acid | grams | 403.01 | 161.20 | 154.48 | 147.76 | 3566.76 | 4800.00 |
| | wt % | 83.96 | 80.60 | 77.24 | 73.88 | 70.52 | 63.98 |
| Phenolic coating | grams | 76.99 | 30.79 | 29.51 | 28.22 | 681.29 | 0.00 |
| | wt % | 16.04 | 15.40 | 14.75 | 14.11 | 13.47 | 0.00 |
| Urethane coating | grams | 0.00 | 8.01 | 16.01 | 24.01 | 809.75 | 2702.28 |
| | wt % | 0.00 | 4.00 | 8.01 | 12.01 | 16.01 | 36.02 |
| Total coating | grams | 76.99 | 38.80 | 45.52 | 52.23 | 1491.04 | 2702.28 |
| | wt % | 16.04 | 19.40 | 22.76 | 26.12 | 29.48 | 36.02 |
| Wt ratio: citric acid to phenolic coating | | 5.23 | 5.24 | 5.23 | 5.24 | 5.24 | |
| Wt ratio: citric acid to urethane coating | | | 20.12 | 9.65 | 6.15 | 4.40 | 1.78 |
| Wt ratio: citric acid to total coating | | 5.23 | 4.15 | 3.39 | 2.83 | 2.39 | 1.78 |
| RELEASE OF CITRIC ACID FROM CAPSULES | | | | | | | |
| Sample weight | grams | 1.255 | 1.216 | 1.248 | 1.295 | 1.276 | 1.200 |
| water weight | grams | 99.086 | 98.712 | 99.845 | 99.436 | 99.241 | 99.000 |
| citric acid | grams | 1.054 | 0.980 | 0.964 | 0.957 | 0.900 | 0.768 |
| wt ratio: water to citric acid | | 94.036 | 100.717 | 103.578 | 103.931 | 110.288 | 128.947 |

TABLE 2

| RELEASE TIME minutes | CAPSULES citric acid released as weight percent of quantity tested | | | | | |
|---|---|---|---|---|---|---|
| | A | A1 | A2 | A3 | A4 | B |
| 0.00 | 0.00 | 0.00 | 0.00 | 0.00 | 0.00 | 0.00 |
| 5.00 | 36.70 | 15.50 | 6.10 | 2.90 | 1.30 | 4.19 |
| 10.00 | 59.20 | 27.80 | 11.00 | 5.80 | 2.70 | 9.06 |
| 20.00 | 65.80 | 43.70 | 18.60 | 10.40 | 4.80 | 17.14 |
| 30.00 | 71.80 | 54.70 | 24.50 | 13.70 | 6.80 | 23.31 |
| 45.00 | 72.90 | 63.60 | 29.30 | 18.60 | 9.40 | 29.54 |
| 60.00 | 73.10 | 65.40 | 36.50 | 22.40 | 11.40 | 34.59 |
| 90.00 | 77.60 | 77.40 | 48.70 | 30.70 | 16.30 | 41.99 |
| 120.00 | 77.80 | 81.70 | 56.60 | 36.70 | 20.30 | 48.16 |
| 150.00 | | 84.30 | 59.20 | 40.10 | 22.40 | 52.48 |
| 184.00 | | 86.20 | 64.60 | 44.10 | 25.20 | |
| 266.00 | | 88.50 | 71.10 | 51.90 | 31.60 | |
| 300.00 | | | 74.80 | 56.10 | 34.40 | |
| 330.00 | | | 76.20 | 58.10 | 36.40 | |
| 375.00 | | | 79.20 | 62.60 | 40.60 | |
| 444.00 | | | 78.10 | 66.50 | 47.30 | |
| 24 (hours) | 83.20 | 84.50 | 83.40 | 81.50 | 79.40 | |

From Tables 1 and 2 it is seen that all capsules operated to release citric acid. The weight ratio of citric acid to phenolic coating for capsules having a phenolic coating was constant. The weight ratio of citric acid to total coating declined from Capsules A (100% phenolic) to Capsules B (100% urethane).

The rate of acid release was a function of the chemical nature of the coating and the concentration of acid in each capsule. In general, the rate of release of acid decreased as the concentration of acid in each capsule decreased and the concentration of total coating increased, but there are exceptions to the general proposition.

The weight percent release of citric acid from capsules having a phenolic interior coating was substantially the same after a period of about 24 hours regardless of the difference in concentration of citric acid in the capsules.

The weight percent of citric acid released from Capsules A (0% urethane, 16.04% total coating) and Capsules A1 (4% urethane, 19.40% total coating) was a greater than the release from Capsules B (100% urethane, 36.02% total coating).

The weight percent of citric acid released from Capsules A2 (8.01% urethane, 22.26% total coating) varied from being greater than to about similar to the release from Capsules B (100% urethane, 36.02% total coating).

The weight percent of citric acid released from Capsules A3 (12.01% urethane, 26.12% total coating) and Capsules A4 (16.01% urethane, 29.48% total coating) was less than the release from Capsules B (100% urethane, 36.02% total coating).

Example 6

Preparation of Polyurethane Coating C

After the period of standing mentioned in step 1 of Example 2A, 3004.2 grams of the precursor product were combined with about 39 grams of a polyaziridine cross-linker and about 208.7 grams of water. The mixture was stirred for about 10 minutes to thereby prepare 3251.9 grams of polyurethane coating C. An attempt was made to apply polyurethane coating C to sodium chloride.

It was calculated that polyurethane coating C consisted of about 1262.87 grams of solid which was about 40.03 weight percent of the product.

Example 7

A fluidized bed coating apparatus was used to apply polyurethane coating C of Example 6 to a total of 7000.0 grams of 10/50 US mesh sodium chloride. The apparatus and procedure employed are described in Example 3A.

The attempt to coat sodium chloride was not successful. The sodium chloride appeared to interfere with the drying of the coating. Variation of the spray rate failed to improve the drying of the coating. The sodium chloride agglomerated into a solid mass after about 1800 grams of polyurethane coating C was added.

Example 8

An apparatus and procedure similar to those described in Example 1 were employed to prepare Capsules C for testing.

About 500 pounds of sodium chloride having a particle size greater than about 50 mesh (US Sieve Series) were placed in a container of suitable size and heated in an oven to a temperature of about 250° F.

The heated sodium chloride was stirred in an apparatus equipped with a paddle having the capability of mixing and stirring particulate solids. An appropriately sized production pan coater Was employed. The pan coater was started and, while mixing and heating, about 24.0 pounds of powdered uncured phenolic resin and about 6.0 pounds of an atomized wax-free flow additive were added to the mixer containing the heated sodium chloride. The phenolic resin employed was available from Plastic Engineering Company of Sheboygan, Wis., and the flow additive was available from Lonza, Inc. of Fairlawn, N.J. The mixture was heated until it became blocky and then it was allowed to cool until it became free and flowing. The heating, mixing and cooling procedure was repeated until the mixture could be heated to 275° F. without becoming blocky. At this point the phenolic resin was considered to be cured. The resulting material, which weighed about 530 pounds, was passed through a 10 US Mesh screen.

The process employed a total of about 500 pounds of sodium chloride, about 24.0 pounds of uncured phenolic resin and about 6.0 pounds of flow additive. It was, accordingly, calculated that the product of the process, Capsules C, included about 94.34 weight percent active sodium chloride and about 5.66 weight percent cured phenolic resin and flow additive.

Example 9

Preparation of Polyurethane Coating D

An amount of 291.7 pounds of the precursor product were made as described in Example 2A. The precursor product included about 122.62 pounds solids which was about 42.04 weight percent solids.

After the period of standing mentioned in step 1 of Example 2A, the precursor product was combined with about 3.8 pounds of a polyaziridine cross-linker and about 20.3 pounds of water. The mixture was stirred for about 10 minutes to thereby prepare 315.8 pounds of polyurethane coating D.

It was calculated that polyurethane coating D contained about 126.42 pounds of solid which was about 40.03 weight percent of the coating.

Example 10

Application of Polyurethane Coating D to Capsules C

A fluidized bed coating apparatus was used to apply 315.8 pounds of polyurethane coating D to a total of 400 pounds of Capsules C. In this regard, 400 pounds of Capsules C were added to the product bowl of a WSG 120 fluidized bed coater available from Glatt Air Techniques equipped with a top spray insert. The spray head employed was a Schick Model 973 nozzle having three nozzle ports with a 2 mm insert available from Orthos Liquid Systems; Inc. An 80 mesh screen was inserted between the expansion chamber and the filter chamber of the coater.

Capsules C were fluidized in the coating apparatus with air heated to a temperature in the range of from about 90 to about 96° F. Polyurethane coating D was sprayed against the fluidized Capsules C through the spray head. The spray head pressure was about 45 psig, and the spray rate was about 2 pounds per minute. The spray was terminated when all the coating was added. The temperature of the bed was then permitted to increase to a temperature in the range of from about 105 to about 110° F. for about five minutes.

It was calculated that the 315.8 pounds of coating D included a total of about 126.42 pounds of solid which were deposited on the capsules. Accordingly, it was also calculated that Capsules C included about 71.68 weight percent sodium chloride and about 28.32 weight percent total coating. Stated differently, Capsules C included about 71.68 weight percent active sodium chloride, about 4.3 weight percent phenolic inner coating and about 24.02 weight percent polyurethane outer coating.

Example 11

Capsules C were immersed in water to determine the release of sodium chloride from the capsules over a period of time.

A weighed quantity of Capsules C was placed in a weighed quantity of water. The sodium chloride in the sample passed into the water over a period of time. The concentration of sodium chloride in the resulting solution of sodium chloride in water increased with passage of time, wherein the concentration of sodium chloride in solution was determined over intervals of time by measuring the electrical conductivity of the solution with an electrical conductivity meter. The meter had been previously calibrated by measuring the conductivity of solutions having known concentrations of sodium chloride.

The solvent water contained 0.1 weight percent nonylphenol. The tests were conducted at room temperature.

Table 3

Table 3 is a summary of calculated results based on experimental quantities employed in Examples 6-10. The Table 3 also summarize experimental quantities employed in Example 11 and calculated results based on such quantities.

TABLE 3

RELEASE OF SODIUM CHLORIDE FROM CAPSULES C

| ITEMS | weight data | weight percent |
|---|---|---|
| coated sample, grams | 2.0090 | — |
| sodium chloride, grams | 1.4401 | 71.68 |
| phenolic coating, grams | 0.0864 | 4.30 |
| urethane coating, grams | 0.4826 | 24.02 |
| total coating, grams | 0.5689 | 28.32 |
| solvent water, grams | 50.4230 | — |
| wt ratio: solvent water to sodium chloride in sample | 35.0147 | — |

TABLE 3-continued

RELEASE DATA

| RELEASE TIME, minutes | Grams | Percent |
|---|---|---|
| 0 | 0.000 | 0.0 |
| 5 | 0.001 | 0.1 |
| 10 | 0.013 | 0.9 |
| 15 | 0.081 | 5.6 |
| 20 | 0.140 | 9.7 |
| 30 | 0.343 | 23.8 |

From Table 3 it is seen that Capsules C operated to release sodium chloride from a capsule having an inner coat of cured phenolic resin and an outer coat of polyurethane. Comparing the results of Example 7 with the results of Examples 8, 9 and 10 reveals that a thermosetting resin, such as the phenolic inner coating, enabled sodium chloride to be coated with a water dispersion of a solid coating material without any interference caused by the water dispersant.

Example 12

Particles of anhydrous ammonium chloride were mixed with an uncured phenolic resin. The mixture of ammonium chloride and uncured resin was heated to cure the resin to thereby produce capsules consisting of ammonium chloride coated by the cured resin. For purposes of identification, these capsules having a single coating of cured phenolic resin were designated as Capsules D.

Three batches of Capsules D were prepared for testing. Each test batch weighed about 1630 grams, accordingly, a total of about 4890 grams of Capsules D were prepared for subsequent testing.

A four step process was employed to prepare each test batch. In the first step, about 1500 grams of anhydrous ammonium chloride having a particle size in the range of from 20 to about 80 mesh US Sieve Series were heated in an oven to a temperature of about 250° F.

In the second step, the heated ammonium chloride was placed in a 5 quart mixing bowl equipped with a paddle having the capability of mixing and stirring particulate solids. The mixer employed was a Kitchen Aid Model KV25G. The mixer was then started and, while mixing and heating, about 119.13 grams of powdered uncured phenolic resin and about 13.23 grams of an atomized wax-free flow additive were added to the mixer containing the heated ammonium chloride. The phenolic resin employed was available from Plastic Engineering Company of Sheboygan, Wis., and the flow additive was available from Lonza, Inc. of Fairlawn, N.J. The mixture was heated and stirred until it became blocky and then it was allowed to cool until it became free and flowing. The heating, mixing and cooling procedure was repeated until the mixture could be heated to 275° F. without becoming blocky. At this point the phenolic resin was considered to be cured. The resulting material, which weighed about 1632.36 grams, was passed through a 10 US Mesh screen which produced a finished product weighing about 1580 grams.

In the third step, the 1580 gram product from the second step was heated to a temperature of about 240° F. at which point the procedure of the second step was repeated except that 66.75 grams of powdered uncured phenolic resin and about 7.41 grams of flow additive were employed. Upon curing, the resulting material, which weighed about 1654.16 grams, was passed through a 10 US Mesh screen which produced a finished product weighing about 1570 grams.

In the fourth step, the 1570 gram product from the third step was heated to a temperature of about 240° F. at which point the procedure of the second step was repeated except that 71.28 grams of powdered uncured phenolic resin and about 7.42 grams of flow additive were employed. Upon curing, the resulting material, which weighed about 1648.70 grams, was passed through a 10 US Mesh screen which produced a finished product weighing about 1630 grams.

It is evident that the process employed a total of about 1500 grams of ammonium chloride, about 257.16 grams of uncured phenolic resin and about 28.06 grams of flow additive. It was calculated that the product of the four-step process, Capsules D, included about 84.02 weight percent ammonium chloride and about 15.98 weight percent cured phenolic resin and flow additive.

Example 13A

This example describes the process employed to make a liquid dispersion of solids containing a cross-linked acrylic and silica particles. For purposes of identification, the product of the process is referred to as acrylic coating E.
Preparation of Acrylic Coating E
1. About 2885.0 grams of water, about 69.6 grams of silicone defoamer and about 104.3 grams of silicone surface additive were mixed with mild agitation in a 2 gallon bucket until the surfactants were dispersed in the mixture. The defoamer was identified as BYK-024 and the surface additive was identified as BYK-333, respectively, with each being available from BYK-Chemie.

At that point the dispersion was mixed with a high shear mixer while about 4061.3 grams of 5-micron silica was slowly added to the mass of material. Mixing was continued until the silica was completely dispersed. The high shear mixer employed was available from Charles Ross and Sons Mixer Company, and the silica was available from US. Silica under the trademark MIN-U-SIL 5.

The mixture of water and silica was placed in a 5-gallon pail. An air mixer was employed to stir the mixture in the pail at a rate sufficient to form a vortex while a quantity of about 9,972.3 grams of a polyacrylate emulsion commercially available from Johnson Polymers, Inc. under the trade name JONCRYL was added. After about 5 minutes of mixing, 539.1 grams of a wax emulsion available from Michelman, Inc., under the trade name MICHEMLUBE was added. A mixture of a polyacrylate emulsion with silica and the use therefor is disclosed in U.S. Pat. No. 5,373,901 to Norman et al.

After about 5 minutes of mixing, 305.2 grams of coalescent solvent, GLYCOL ETHER PNB available from Chem Central, was added. The mixing rate was adjusted to maintain the vortex. After about 30 minutes of mixing, about 63.1 grams of 29 weight percent aqueous ammonia was added and mixing was continued for about 30 minutes. The resulting precursor product was set aside and allowed to stand at least over night.

It is evident that preparation of the precursor product employed about 18000 grams of ingredients, of which about 9467.9 grams were considered to be solids. It was, accordingly, calculated that the product included about 52.6 weight percent solids.
2. After the period of standing, 2679.2 grams of the precursor product were combined with about 75.7 grams of a polyaziridine cross-linker and about 545.1 grams of water. The mixture was stirred for about 10 minutes to thereby prepare 3300.0 grams of acrylic coating E. Acrylic coating E was applied to Capsules D.

It was calculated that acrylic coating E consisted of about 1484.94 grams of solid which was about 43.67 weight percent of the product.

Example 13B

This example describes the process employed to make a liquid dispersion of solids containing a cross-linked acrylic acid and silica particles. For purposes of identification, the product of the process is referred to as acrylic coating F.
Preparation of Acrylic Coating F
After the period of standing, 3419.8 grams of the precursor product from Step 1 of Example 13A were combined with about 95.9 grams of a polyaziridine cross-linker and about 694.8 grams of water. The mixture was stirred for about 10 minutes to thereby prepare 4210.5 grams of acrylic coating F. Acrylic coating F was applied to ammonium chloride.

It was calculated that acrylic coating F consisted of about 1894.71 grams of solid which was about 45 weight percent of the product.

Example 14

Capsules D were contacted with successive quantities of acrylic coating E to place a coating of cross-linked acrylic on Capsules D. The acrylic coated products are referred to herein as Capsules D1, D2, D3 and D4. It is clear that Capsules D1, D2, D3 and D4 included a core of ammonium chloride, an inner coating of cured phenolic resin and an outer coating of cross-linked acrylic.
Application of Acrylic Coating E to Capsules D
A. Capsules D1

A fluidized bed coating apparatus was used to apply 2947.4 grams of acrylic coating E to a total of 4500 grams of Capsules D. In this regard, 4500 grams of Capsules D were added to the product bowl of a WSG 5 fluidized bed coater available from Glatt Air Techniques equipped with a top spray insert. The spray head employed was a Schick Model 970 nozzle having a 1.2 mm insert available from Orthos Liquid Systems, Inc. An 80 mesh screen was inserted between the expansion chamber and the filter chamber of the coater.

Capsules D were fluidized in the coating apparatus with air heated to a temperature in the range of from about 100 to about 105° F. Acrylic coating E was sprayed against the fluidized Capsules D through the spray head. The spray head pressure was about 37 psig, and the spray rate was about 40 grams per minute.

The spray was terminated when a total of 1363.6 grams of acrylic coating E had passed through the spray head. At this point 300 grams of the coated capsules, now referred to as Capsules D1, were removed from the coating apparatus for future testing.

It was calculated that the 1363.6 grams of coating included a total of about 595.48 grams of solid which were deposited on the capsules. Accordingly, it was also calculated that Capsules D1 included about 74.201 weight percent active ammonium chloride and about 25.799 weight percent total coating. Stated differently, Capsules D1 included about 74.201 weight percent active ammonium chloride, about 14.112 weight percent phenolic inner coating and about 11.687 weight percent acrylic outer coating.

After removal of the 300 gram sample of Capsules D1, the coating apparatus contained a total of about 4795.484 grams of Capsules D1.
B. Capsules D2
The quantity of Capsules D1 remaining in the coating apparatus were then sprayed with acrylic coating E to thereby produce Capsules D2. The apparatus and conditions employed to produce Capsules D1 were used to produce Capsules D2, but the spray rate was increased to 70 grams per minute.

The spray was terminated when a total of 509.4 grams of acrylic coating E had passed through the spray head. At this point 300 grams of the coated capsules, now referred to as Capsules D2, were removed from the coating apparatus for future testing.

It was calculated that the 509.4 grams of coating included a total of about 222.45 grams of solid which were deposited on the capsules. Accordingly, it was also calculated that Capsules D2 included about 70.9 weight percent active ammonium chloride acid and about 29.1 weight percent total coating. Stated differently, Capsules D2 included about 70.9 weight percent active ammonium chloride, about 13.5 weight percent phenolic inner coating and about 15.6 weight percent acrylic outer coating.

After removal of the 300 gram sample of Capsules D2, the coating apparatus contained a total of about 4717.94 grams of Capsules D2.

C. Capsules D3

The quantity of Capsules D2 remaining in the coating apparatus were then sprayed with acrylic coating E to thereby produce Capsules D3. The apparatus and conditions employed to produce Capsules D2 were used to produce Capsules D3.

The spray was terminated when a total of 527 grams of acrylic coating E had passed through the spray head. At this point 300 grams of the coated capsules, now referred to as Capsules D3, were removed from the coating apparatus for future testing.

It was calculated that the 527 grams of coating included a total of about 230.14 grams of solid which were deposited on the capsules. Accordingly, it was also calculated that Capsules D3 included about 67.6 weight percent ammonium chloride and about 32.4 weight percent total coating. Stated differently, Capsules D3 included about 67.6 weight percent ammonium chloride, about 12.86 weight percent phenolic inner coating and about 19.54 weight percent acrylic outer coating.

After removal of the 300 gram sample of Capsules D3, the coating apparatus contained a total of about 4648.08 grams of Capsules D3.

D. Capsules D4

The quantity of Capsules D3 remaining in the coating apparatus were then sprayed with acrylic coating E to thereby produce Capsules D4. The apparatus and conditions employed to produce Capsules D3 were used to produce Capsules D4.

The spray was terminated when a total of 547.4 grams of acrylic coating E had passed through the spray head. The temperature of the bed was permitted to increase to a temperature in the range of from about 110 to about 115° F. for about five minutes. At this point 300 grams of the coated capsules, now referred to as Capsules D4, were removed from the coating apparatus for future testing.

It was calculated that the 547.4 grams of coating included a total of about 239.05 grams of solid which were deposited on the capsules. Accordingly, it was also calculated that Capsules D4 included about 64.29 weight percent active ammonium chloride and about 35.71 weight percent total coating. Stated differently, Capsules D4 included about 64.29 weight percent active ammonium chloride, about 12.23 weight percent phenolic inner coating and about 23.48 weight percent acrylic outer coating.

After removal of the 300 gram sample of Capsules D4, the coating apparatus contained a total of about 4587.13 grams of Capsules D4.

Example 15

Application of Acrylic Coating F to Ammonium Chloride

A fluidized bed coating apparatus was used to apply acrylic coating F to ammonium chloride. In this regard, 4210.5 grams of acrylic coating F was applied to 6000 grams of ammonium chloride by employing the apparatus and procedure described in Example 14A.

It was calculated that the 4210.5 grams of coating F included a total of about 1894.72 grams of solid which were deposited on the ammonium chloride. Accordingly, it was also calculated that the coated product, referred to as Capsules E, included about 76 weight percent ammonium chloride and about 24 weight percent total coating. Stated differently, Capsules E included about 76 weight percent active ammonium chloride and about 24 weight percent acrylic outer coating.

Example 16

Capsules D, D1, D2, D3, D4 and E were immersed in water to determine the release of ammonium chloride from the capsules over a period of time.

Samples of each of Capsules D, D1, D2, D3, D4 and E were placed in water. The ammonium chloride in each sample passed into the water over a period of time. The concentration of ammonium chloride in the resulting solutions of ammonium chloride in water increased with passage of time, wherein the concentration of ammonium chloride in a solution was determined over intervals of time by measuring the electrical conductivity of the solution with an electrical conductivity meter. The meter had been previously calibrated by measuring the conductivity of solutions having known concentrations of ammonium chloride.

The water solvent contained 0.1 Weight percent nonylphenol. The tests were conducted at room temperature.

Tables

Table 4 is a summary of calculated results based on experimental quantities employed in Examples 12-15. The contents of Table 4 also summarize experimental quantities employed in Example 16 and calculated results based on such quantities. Table 5 is a summary of ammonium chloride released from the capsules as a weight percent of ammonium chloride in the samples tested.

TABLE 4

| DATA | | CAPSULES | | | | | |
|---|---|---|---|---|---|---|---|
| | | D | D1 | D2 | D3 | D4 | E |
| Total Grams (solids) | | 390.00 | 300.00 | 300.00 | 300.00 | 4887.13 | 7894.72 |
| Ammonium chloride | grams | 327.68 | 222.60 | 212.70 | 202.80 | 3141.94 | 5999.99 |
| | wt % | 84.02 | 74.20 | 70.90 | 67.60 | 64.29 | 76.00 |
| Phenolic coating | grams | 62.32 | 42.33 | 40.50 | 38.58 | 597.70 | 0.00 |
| | wt % | 15.98 | 14.11 | 13.50 | 12.86 | 12.23 | 0.00 |
| Acrylic coating | grams | 0.00 | 35.07 | 46.80 | 58.62 | 1147.50 | 1894.73 |
| | wt % | 0.00 | 11.69 | 15.60 | 19.54 | 23.48 | 24.00 |

TABLE 4-continued

|  |  | CAPSULES |  |  |  |  |  |
| --- | --- | --- | --- | --- | --- | --- | --- |
| DATA |  | D | D1 | D2 | D3 | D4 | E |
| Total coating | grams | 62.32 | 77.40 | 87.30 | 97.20 | 1745.19 | 1894.73 |
|  | wt % | 15.98 | 25.80 | 29.10 | 32.40 | 35.71 | 24.00 |
| Wt ratio: ammonium chloride to phenolic coating |  | 5.26 | 5.26 | 5.25 | 5.26 | 5.26 |  |
| Wt ratio: ammonium chloride to acrylic coating |  |  | 6.35 | 4.54 | 3.46 | 2.74 | 3.17 |
| Wt ratio: ammonium chloride to total coating |  | 5.26 | 2.88 | 2.44 | 2.09 | 1.80 | 3.17 |
| RELEASE OF AMMONIUM CHLORIDE FROM CAPSULES | | | | | | | |
| Sample weight | grams |  | 1.606 | 1.602 | 1.600 | 1.601 | 2.027 |
| water weight | grams |  | 98.470 | 98.520 | 98.436 | 98.596 | 48.022 |
| ammonium chloride | grams | 0.000 | 1.192 | 1.136 | 1.082 | 1.029 | 1.541 |
| wt ratio: water to ammonium chloride |  |  | 82.633 | 86.739 | 91.010 | 95.791 | 31.173 |

TABLE 5

| RELEASE TIME | CAPSULES ammonium chloride released as weight percent of quantity tested | | | | | |
| --- | --- | --- | --- | --- | --- | --- |
| minutes | D | D1 | D2 | D3 | D4 | E |
| 0.00 |  | 0.00 | 0.00 | 0.00 | 0.00 |  |
| 5.00 |  | 18.90 |  | 9.20 | 4.00 |  |
| 10.00 |  | 25.40 | 13.20 | 3.90 | 4.10 | 84.20 |
| 15.00 |  | 29.50 | 15.60 | 7.80 | 5.10 |  |
| 20.00 |  | 33.50 | 18.70 | 10.90 | 6.00 |  |
| 30.00 |  | 39.00 | 19.90 | 16.10 | 8.50 | 88.60 |
| 40.00 |  | 43.90 | 24.90 | 18.60 | 10.70 |  |
| 50.00 |  | 47.00 | 27.90 | 18.90 | 15.50 |  |
| 60.00 |  | 51.30 | 29.60 | 20.60 | 14.80 | 93.80 |

From Tables 4 and 5 it is seen that all capsules operated to release ammonium chloride, however, no release control was obtained for Capsules D which did have a phenolic coating, but which did not have an acrylic outer coating. The weight ratio of ammonium chloride to phenolic coating for capsules having a phenolic coating was constant. The weight ratio of ammonium chloride to acrylic coating declined for capsules which included an inner phenolic coating and an outer acrylic coating.

The rate of ammonium chloride release for capsules D1, D2, D3 and D4, which had a phenolic inner coating and an acrylic outer coating, was a function of the chemical nature of the coating and the concentration of ammonium chloride in each capsule. In this regard, the rate of release of ammonium chloride decreased as the concentration of ammonium chloride in each capsule decreased and the concentration of total coating increased. To be more specific, the rate of release decreased as the concentration of phenolic decreased and the concentration of acrylic increased.

The rate of ammonium chloride release from Capsules E, which had no phenolic coating, but which did have an acrylic coating varied from a factor of about 1.83 to a factor of about 20.5 times greater than the release rate from capsules, i.e. D1, D2, D3 and D4, having both a phenolic coating and an acrylic coating.

Having described the invention that which is claimed is:
1. A capsule having a hollow interior,
   said capsule consisting of a water-soluble, particulate reactive chemical enclosed in said hollow interior by a wall which is permeable to water, but which is not water soluble;
   said wall is comprised of a first coating
   wherein
   said first coating is a heat-cured first chemical composition whereby said capsule having said first coating is dry, flowable and not sticky; and
   wherein
   said first chemical composition is selected from the group consisting of phenolic, epoxy and melamine thermosetting synthetic resins.
2. The capsule of claim 1 wherein said thermosetting resin is a phenolic resin.
3. The capsule of claim 2 wherein said phenolic resin is the reaction product of phenol and formaldehyde.
4. The capsule of claim 1 wherein said thermosetting resin is an epoxy resin.
5. The capsule of claim 4 wherein said epoxy resin is the reaction product of epichlorohydrin, bisphenol A and diethylenetriamine.
6. The capsule of claim 1 wherein said thermosetting resin is a melamine resin.
7. The capsule of claim 6 wherein said melamine resin is the reaction product of melamine, formaldehyde and methanol.
8. The capsule of claim 1 further comprising a second coating, wherein the interior of said first coating is in direct contact with said reactive chemical in said hollow interior of said capsule, the exterior of said first coating is in direct contact with the interior of said second coating and said second coating is a second chemical composition different from said first chemical composition wherein said second chemical composition is a polyurethane-vinyl polymer dispersion prepared by the simultaneous polymerization of a vinyl monomer and chain extension of an isocyanate-terminated polyurethane prepolymer in the presence of water.
9. The capsule of claim 8 wherein said thermosetting resin is a phenolic resin.
10. The capsule of claim 9 wherein said phenolic resin is the reaction product of phenol and formaldehyde.
11. The capsule of claim 8 wherein said thermosetting resin is an epoxy resin.
12. The capsule of claim 11 wherein said epoxy resin is the reaction product of epichlorohydrin, bisphenol A and diethylenetriamine.
13. The capsule of claim 8 wherein said thermosetting resin is a melamine resin.
14. The capsule of claim 13 wherein said melamine resin is the reaction product of melamine, formaldehyde and methanol.
15. The capsule of claim 1 further comprising a second coating, wherein the interior of said first coating is in direct contact with said reactive chemical in said hollow interior of said capsule, the exterior of said first coating is in direct contact with the interior of said second coating and said second coating is a second chemical composition different from said first chemical composition wherein said second chemical composition is a partially hydrolyzed acrylic polymer cross-linked with one of an aziridine prepolymer or a carbodiimide.

16. The capsule of claim 15 wherein said thermosetting resin is a phenolic resin.

17. The capsule of claim 16 wherein said phenolic resin is the reaction product of phenol and formaldehyde.

18. The capsule of claim 15 wherein said thermosetting resin is an epoxy resin.

19. The capsule of claim 18 wherein said epoxy resin is the reaction product of epichlorohydrin, bisphenol A and diethylenetriamine.

20. The capsule of claim 15 wherein said thermosetting resin is a melamine resin.

21. The capsule of claim 20 wherein said melamine resin is the reaction product of melamine, formaldehyde and methanol.

* * * * *